United States Patent [19]

Tantau

[11] Plant 4,799

[45] Jan. 19, 1982

[54] ROSE PLANT

[75] Inventor: Mathias Tantau, Uetersen, Fed. Rep. of Germany

[73] Assignee: Jackson & Perkins Company, Medford, Oreg.

[21] Appl. No.: 176,599

[22] Filed: Aug. 8, 1980

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having orange-yellow to yellow flowers borne on medium length stems and having a light licorice fragrance.

1 Drawing Figure

This present invention relates to a new and distinct variety of rose plant of the hybrid tea class which was originated by me by crossing the variety Minigold, U.S. Plant Pat. No. 3,103, with the variety Precilla, U.S. Plant Pat. No. 3,726.

The primary objective of this breeding was to produce a new rose variety especially suitable for the production of cut flowers in a greenhouse, producing clear yellow flowers on stems long enough for use in the florist shops. This objective was substantially achieved along with other desirable improvements as evidenced by the following unique combination of characteristics which are outstanding in the new variety and which distinguish it from its parents as well as from all other varieties of which I am aware:

1. Bud color of yellow-orange opening to a slightly lighter open flower.
2. Medium length stems, useful for florists.
3. Average thorniness.
4. Medium green foliage of average resistance to rose powdery mildew.
5. Light licorice-like fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Minigold, U.S. Plant Pat. No. 3,103.

*Pollen parent.*—Precilla, U.S. Plant Pat. No. 3,726.

Classification:

*Botanical.*—Rosa hybrid.

*Commercial.*—Hybrid Tea.

FLOWER

Observations made from specimens grown in a greenhouse at Irvine, Calif., in January, 1980.

Blooming habit: continuous.

Bud:

*Size.*—1" to 1½" when petals start to unfurl.

*Form.*—Pointed ovoid.

*Color.*—When sepals first divide, Yellow-Orange 21B with slightly lighter areas; when half blown, upper side of petals very near Yellow-Orange 15B; lower side of petals near Yellow-Orange 15B.

*Sepals.*—Color: Outer surface Green 141C to 141D near midrib; three appendaged sepals lightly appendaged; two unappendaged sepals hairy edged.

*Receptacle.*—Color: near green 141C. Shape: funnel. Size: large, long. Surface: glaucescent.

*Peduncle.*—Length: medium. Surface: glandular and pilosulous. Color: light green. Strength: erect, sometimes bending, slender.

*Opening.*—Opens to urn-shaped bud, then high-centered open flower sometimes has divided center.

Bloom:

*Size.*—Large. Average open size 4½".

*Borne.*—Singly.

*Stems.*—Long, normal to weak.

*Form.*—When first open, high centered. Permanence: outer petal edges slightly curled.

*Petalage.*—Number of petals under normal conditions: 40.

*Color.*—Center of flower: upper side of petals near Yellow-Orange 15B. Reverse side of petals Yellow-Orange 15B. Base of petals at point of attachment Yellow-Orange 21B. General tonality from a distance Yellow-Orange 15B.

*Variegations.*—Occasionally a green vegetative segment appears in outer petals.

*Discoloration.*—General tonality at end of first day, Yellow-Orange 15B; third day, lightly fading to 15C and 15D.

*Fragrance.*—Slight, licorice-like.

Petals:

*Texture.*—Thick.

*Shape.*—Round.

*Form.*—Tips slightly recurved.

*Arrangement.*—Roughly imbricated. Petaloids in center: few.

*Persistence.*—Drop off cleanly.

*Lastingness.*—On the plant, long. As cut flower, long.

Reproductive parts:

*Anthers.*—Small, many. Color: yellow. Arrangement: regular around styles.

*Filaments.*—Color: yellow.

*Pollen.*—Gold yellow.

*Styles.*—Color: white — basal half; pink — distal half.

*Stigmas.*—Color: yellow.

PLANT

Form: Bush.

Growth: Very vigorous, upright, branching.

Foliage: Number of leaflets on normal mid-stem leaves: 5, occasionally 7.

*Size.*—Medium.

*Quantity.*—Normal.

*Color.*—New foliage: Green 141D with shadings of maroon, especially near leaflet edges. Old foliage: Green 136B under normal conditions.

Leaflets:

*Shape.*—Oval pointed.

*Texture.*—Leathery.

*Edge.*—Serrated.

*Serration.*—Single, small.

*Petiole.*—Rachis. Color: green. Underside: Few large prickles. Upper ridges slightly pilosulous and with stipitate glands.

*Stipules.*—Long, bearded.

*Disease resistance.*—Normally resistant to mildew under normal growing conditions at Irvine, Calif.

Wood:

*New wood.*—Color: light green. Bark: smooth.

Old wood.—Color: green. Bark: smooth.

Prickles:

*Quantity.*—On main stalks from base: ordinary. On laterals from stalk: ordinary.

*Form.*—Long base, hooked downward.

*Color when young.*—Green.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of orange-yellow to yellow flowers on medium length stems, average thorniness and a light licorice fragrance.

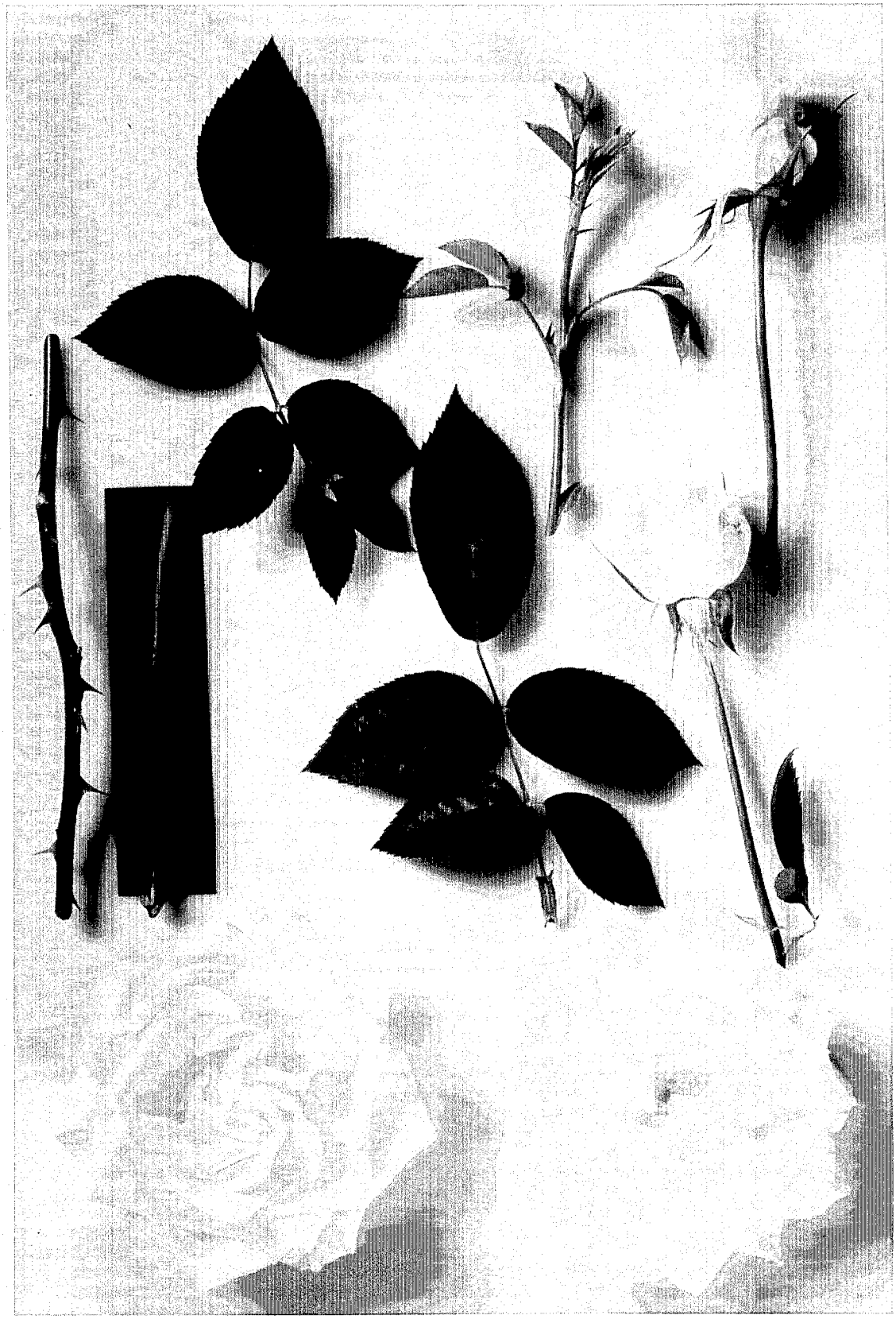

* * * * *